US012207849B2

(12) United States Patent
Harder et al.

(10) Patent No.: US 12,207,849 B2
(45) Date of Patent: Jan. 28, 2025

(54) SET SCREW FOR FEMORAL NAIL

(71) Applicant: Stryker European Operations Limited, Carrigtwohill (IE)

(72) Inventors: Lasse Harder, Schönberg (DE); André Wilke, Kiel (DE)

(73) Assignee: Stryker European Operations Limited, Carrigtwohill (IE)

( * ) Notice: Subject to any disclaimer, the term of this patent is extended or adjusted under 35 U.S.C. 154(b) by 253 days.

(21) Appl. No.: 17/909,108

(22) PCT Filed: Mar. 3, 2021

(86) PCT No.: PCT/IB2021/000117
§ 371 (c)(1),
(2) Date: Sep. 2, 2022

(87) PCT Pub. No.: WO2021/176274
PCT Pub. Date: Sep. 10, 2021

(65) Prior Publication Data
US 2023/0101690 A1 Mar. 30, 2023

Related U.S. Application Data

(60) Provisional application No. 63/065,208, filed on Aug. 13, 2020, provisional application No. 62/986,138, filed on Mar. 6, 2020.

(51) Int. Cl.
*A61B 17/74* (2006.01)
(52) U.S. Cl.
CPC .................. *A61B 17/744* (2013.01)

(58) Field of Classification Search
CPC .................................................. A61B 17/744
(Continued)

(56) References Cited

U.S. PATENT DOCUMENTS 3,433,220 A 3/1969 Zickel
4,776,330 A 10/1988 Chapman et al.
(Continued)

FOREIGN PATENT DOCUMENTS

CA 2986540 A1 12/2016
EP 0257118 B1 6/1990
(Continued)

OTHER PUBLICATIONS

European Examination Report for Application No. 12705227.2 dated May 5, 2015.
(Continued)

*Primary Examiner* — Eduardo C Robert
*Assistant Examiner* — Tara Rose E Carter
(74) *Attorney, Agent, or Firm* — Lerner David LLP

(57) ABSTRACT

A set screw for use in an intramedullary fracture fixation device having a longitudinal axis includes a housing and a set screw. The set screw may include a body with an external thread and an elastic member extending from the body, the elastic member having an uncompressed condition and a compressed condition. The housing may include a sidewall partially surrounding the longitudinal axis that defines a cavity for receiving the set screw such that when the set screw is at least partially disposed within the cavity and in the uncompressed condition, the set screw is secured to the housing and rotatable relative to the housing.

16 Claims, 12 Drawing Sheets

(58) Field of Classification Search
USPC .................................................. 606/62–68
See application file for complete search history.

(56) References Cited

U.S. PATENT DOCUMENTS

| | | | |
|---|---|---|---|
| 5,032,125 | A | 7/1991 | Durham et al. |
| 5,176,681 | A | 1/1993 | Lawes et al. |
| 5,454,813 | A | 10/1995 | Lawes |
| 6,221,074 | B1 | 4/2001 | Cole et al. |
| 6,296,645 | B1 | 10/2001 | Hover et al. |
| 6,402,753 | B1 | 6/2002 | Cole et al. |
| 6,406,477 | B1 | 6/2002 | Fujiwara |
| 6,443,954 | B1 | 9/2002 | Bramlet et al. |
| 6,648,889 | B2 | 11/2003 | Bramlet et al. |
| 6,835,197 | B2 | 12/2004 | Roth et al. |
| 6,855,146 | B2 | 2/2005 | Frigg et al. |
| 6,921,400 | B2 | 7/2005 | Sohngen |
| 6,926,719 | B2 | 8/2005 | Sohngen et al. |
| 7,018,380 | B2 | 3/2006 | Cole |
| 7,041,104 | B1 | 5/2006 | Cole et al. |
| 7,182,765 | B2 | 2/2007 | Roth et al. |
| 7,306,600 | B2 | 12/2007 | Roth et al. |
| 7,591,819 | B2 | 9/2009 | Zander et al. |
| 7,601,153 | B2 | 10/2009 | Shinjo et al. |
| 7,763,023 | B2 | 7/2010 | Gotfried |
| 7,867,231 | B2 | 1/2011 | Cole |
| 8,092,454 | B2 | 1/2012 | Sohngen |
| 8,100,911 | B2 | 1/2012 | Yamazaki et al. |
| 8,157,801 | B2 | 4/2012 | Doubler et al. |
| 8,157,802 | B2 | 4/2012 | Elghazaly et al. |
| 8,172,841 | B2 | 5/2012 | Defossez |
| 8,303,590 | B2 | 11/2012 | Elghazaly et al. |
| 8,486,071 | B2 | 7/2013 | Jensen et al. |
| 8,491,584 | B1 | 7/2013 | Fagan |
| 8,702,707 | B2 | 4/2014 | Sohngen |
| 8,808,293 | B2 | 8/2014 | Buettler et al. |
| 8,840,675 | B2 | 9/2014 | Song |
| 8,906,023 | B2 | 12/2014 | Matityahu et al. |
| 8,915,917 | B2 | 12/2014 | Doherty et al. |
| 9,060,808 | B2 | 6/2015 | Overes et al. |
| 9,072,552 | B2 | 7/2015 | Simon et al. |
| 9,084,643 | B2 | 7/2015 | Mikhail et al. |
| 9,149,316 | B2 | 10/2015 | Appenzeller et al. |
| 9,220,544 | B2 | 12/2015 | Matityahu et al. |
| 9,295,504 | B2 | 3/2016 | Haidukewych et al. |
| 9,433,448 | B2 | 9/2016 | Ehmke et al. |
| 9,433,449 | B2 | 9/2016 | Vega et al. |
| 9,463,054 | B2 | 10/2016 | Mueckter |
| 9,526,542 | B2 | 12/2016 | Ehmke |
| 9,597,128 | B2 | 3/2017 | Boileau et al. |
| 9,757,169 | B2 | 9/2017 | Boraiah |
| 9,861,418 | B2 | 1/2018 | Matityahu et al. |
| 9,883,895 | B2 | 2/2018 | Mikhail et al. |
| 9,895,177 | B2 | 2/2018 | Hientzsch et al. |
| 9,918,757 | B2 | 3/2018 | Roth et al. |
| 9,936,989 | B2 | 4/2018 | Halder |
| 9,943,346 | B2 | 4/2018 | Elghazaly et al. |
| 10,092,334 | B2 | 10/2018 | Sato et al. |
| 2002/0032445 | A1 | 3/2002 | Fujiwara |
| 2002/0107578 | A1 | 8/2002 | Speitling et al. |
| 2002/0156473 | A1 | 10/2002 | Bramlet et al. |
| 2004/0127898 | A1 | 7/2004 | Adam |
| 2005/0069397 | A1 | 3/2005 | Shavit et al. |
| 2005/0143739 | A1 | 6/2005 | Shinjo et al. |
| 2005/0203510 | A1 | 9/2005 | Sohngen |
| 2006/0156473 | A1 | 7/2006 | Chambers et al. |
| 2006/0200160 | A1 | 9/2006 | Border et al. |
| 2007/0049938 | A1 | 3/2007 | Wallace et al. |
| 2007/0049939 | A1 | 3/2007 | Wallace et al. |
| 2007/0049940 | A1 | 3/2007 | Wallace et al. |
| 2007/0233100 | A1 | 10/2007 | Metzinger |
| 2008/0140077 | A1 | 6/2008 | Kebaish |
| 2008/0294164 | A1* | 11/2008 | Frank .................. A61B 17/744 606/301 |
| 2008/0294203 | A1 | 11/2008 | Kovach et al. |
| 2009/0048600 | A1 | 2/2009 | Matityahu et al. |
| 2009/0248025 | A1 | 10/2009 | Haidukewych et al. |
| 2010/0249781 | A1 | 9/2010 | Haidukewych et al. |
| 2010/0249852 | A1 | 9/2010 | Brumfield et al. |
| 2011/0054474 | A1 | 3/2011 | Metzinger et al. |
| 2011/0196370 | A1 | 8/2011 | Mikhail |
| 2011/0196372 | A1 | 8/2011 | Murase |
| 2012/0197255 | A1 | 8/2012 | Elghazaly |
| 2012/0253410 | A1 | 10/2012 | Taylor et al. |
| 2013/0041414 | A1 | 2/2013 | Epperly et al. |
| 2013/0158601 | A1 | 6/2013 | Stone et al. |
| 2014/0012259 | A1 | 1/2014 | Matityahu et al. |
| 2014/0058392 | A1 | 2/2014 | Mueckter et al. |
| 2014/0088595 | A1 | 3/2014 | Mueckter et al. |
| 2014/0094802 | A1 | 4/2014 | Simon et al. |
| 2014/0330174 | A1 | 11/2014 | Warlick et al. |
| 2014/0330274 | A1 | 11/2014 | Matityahu et al. |
| 2015/0209090 | A1 | 7/2015 | Simon et al. |
| 2015/0272634 | A1 | 10/2015 | Mikhail et al. |
| 2016/0199109 | A1* | 7/2016 | Zehtab .............. A61B 17/7233 606/64 |
| 2016/0213409 | A1 | 7/2016 | Frank et al. |
| 2016/0296261 | A1 | 10/2016 | Elghazaly |
| 2016/0310176 | A1 | 10/2016 | Van Dyke et al. |
| 2017/0014167 | A1 | 1/2017 | Ehmke |
| 2018/0146992 | A1 | 5/2018 | Prien et al. |
| 2018/0250042 | A1 | 9/2018 | Sato et al. |

FOREIGN PATENT DOCUMENTS

| | | |
|---|---|---|
| EP | 0838199 A1 | 4/1998 |
| EP | 1175872 A2 | 1/2002 |
| EP | 1415605 A1 | 5/2004 |
| EP | 1547534 A2 | 6/2005 |
| EP | 2253285 A1 | 11/2010 |
| EP | 2730243 A1 | 5/2014 |
| FR | 2965471 A1 | 4/2012 |
| JP | H02-21859 A | 1/1990 |
| JP | 3307805 B2 | 7/2002 |
| JP | 2005205201 A | 8/2005 |
| JP | 2005278819 A | 10/2005 |
| JP | 2009148318 A | 7/2009 |
| JP | 2012507355 A | 3/2012 |
| JP | 2014064613 A | 4/2014 |
| JP | 2014512857 A | 5/2014 |
| JP | 2015507487 A | 3/2015 |
| KR | 100953149 B1 | 4/2010 |
| WO | 02067794 A1 | 9/2002 |
| WO | 02098330 A2 | 12/2002 |
| WO | 03032852 A2 | 4/2003 |
| WO | 03094763 A1 | 11/2003 |
| WO | 2007038560 A1 | 4/2007 |
| WO | 2008001324 A2 | 1/2008 |
| WO | 2012107056 A1 | 8/2012 |
| WO | 2013090859 A1 | 6/2013 |
| WO | 2013134387 A1 | 9/2013 |
| WO | 2015052841 A1 | 4/2015 |
| WO | 2016190842 A1 | 12/2016 |
| WO | 2019024741 A1 | 2/2019 |

OTHER PUBLICATIONS

Gamma3 Long Nail R2, Copyright date 2004, pp. 1-52.
Heineman, et al., "Intra-abdominal Migration of a Lag Screw in Gamma Nailing: Report of a Case", J Orthop Trauma, Dec. 2010, vol. 24, No. 12, pp. e119-e122.
Horas, et al., "Mediale Schenkelhalsschraubendislokation nach Gammanagelosteosynthese einer pertrochantaren Femurmetastase", Feb. 2008, p. 746-748 (English translation of Abstract provided).
International Search Report for Application No. PCT/EP2011/000585 dated Jun. 27, 2011.
International Search Report for Application No. PCT/EP2012/000577 dated May 31, 2012.
International Search Report for PCT/IB2021/000114 mailed Aug. 11, 2021; 7 pages.
International Search Report for PCT/IB2021/000117 mailed Aug. 11, 2021; 7 pages.

(56) References Cited

OTHER PUBLICATIONS

Japanese Office Action for Application No. 2013-552885 dated Aug. 25, 2015.
Li, et al., "Medical pelvic migration of the lag screw in a short gamma nail after hip fracture fixation: a case report and review of the literature", Journal of Orthopaedic Surgery and Research, Aug. 2010, 5:62, pp. 1-7.
Partial Search Report including the Provisional Opinion for International Application No. PCT/IB2021/000114, date of mailing Jun. 21, 2021, 10 pages.
Partial Search Report including the Provisional Opinion for International Application No. PCT/IB2021/000117, date of mailing Jun. 21, 2021, 13 pages.
Synthes, "Titanium Trochanteric Fixation Nail System-Screw Option. For intramedullary fixation of proximal femur fractures.", Copyright date 2010, pp. 1-67.

* cited by examiner

SET SCREW FOR FEMORAL NAIL

CROSS-REFERENCE TO RELATED APPLICATIONS

The present application is a national phase entry under 35 U.S.C. § 371 of International Application No. PCT/IB2021/000117, filed Mar. 3, 2021, published in English, which claims the benefit of the filing date of U.S. Provisional Application No. 63/065,208, filed Aug. 13, 2020, and U.S. Provisional Application No. 62/986,138, filed Mar. 6, 2020, both applications entitled Set Screw for Femoral Nail, the disclosures of all of which are hereby incorporated herein by reference.

BACKGROUND OF THE DISCLOSURE

The present disclosure relates generally to intramedullary devices for internal fixation of a fractured long bone.

Femoral fractures often occur in the femoral neck and trochanteric regions. Fractures of this type are commonly treated with intramedullary intertrochanteric fracture fixation devices that include an intramedullary rod (sometimes referred to as an intramedullary nail or femoral nail) having an angulated opening to receive a neck screw. The neck screw is designed to transfer the load from the femoral head into the shaft of the femoral nail while bridging the fracture line such that the fractured bone portions are compressed together and stabilized during osteogenesis.

Intramedullary nails are intended to be inserted into the medullary canal of the femur over a guidewire. The guidewire aids in retaining proper placement of the fractured bone portions while the nail is inserted into the medullary canal of the bone. Once the intramedullary nail has reached its intended position within the medullary canal, the guidewire may be removed, thus allowing the neck screw to be inserted through the angulated opening of the femoral nail and into intertrochanteric bone. A fastener such as a set screw is then inserted through an axial bore defined in a proximal portion of the intramedullary nail to fasten the neck screw to the nail.

Postoperative rotational movement of the fractured bone fragments can lead to complications such as shortening of the neck of the femur, which may result in reduced physical function. It is therefore desirable to compress the fracture site intra-operatively and then stabilize the bone portions to minimize their postoperative rotational movement during healing of the bone. It is also sometimes advantageous to allow for limited axial sliding of the neck screw relative to the intramedullary nail to account for load shifting, which may occur, for example, when the weight of a patient is applied to his or her hip.

Despite the improvements that have been made to intramedullary intertrochanteric fracture fixation devices, various shortcomings remain. For example, conventional set screws occlude the axial bore such that the set screw cannot be inserted into the intramedullary nail until after the intramedullary nail has been implanted in the medullary canal of the bone and the guidewire has been removed. This is problematic because fastening the set screw to the neck screw can be a time consuming process when performed intraoperatively as soft tissue often overlaps the proximal end of the axial bore. Reamed bone fragments disposed within the axial bore may further exacerbate the already difficult task of engaging the threading of the set screw with corresponding threading in the femoral nail. Moreover, improper threading of the set screw can damage the threads of the set screw or the intramedullary nail, making the set screw susceptible to backing out, which can lead to postoperative rotation of the fractured bone portions.

BRIEF SUMMARY OF THE DISCLOSURE

In accordance with a first aspect of the present disclosure, a cannulated set screw assembly for use in an intramedullary intertrochanteric fracture fixation device is provided. The cannulated set screw assembly allows a manufacturer or other user to pre-operatively fasten the set screw assembly to corresponding threading within the femoral nail, thereby reducing error and operation time.

The set screw assembly has a longitudinal axis and incudes a set screw and a housing. The set screw may include a body with an external thread and an elastic member extending from the body, the elastic member having an uncompressed condition and a compressed condition. The housing may include a sidewall partially surrounding the longitudinal axis that defines a cavity for receiving the set screw such that when the set screw is at least partially disposed within the cavity, the set screw is secured to the housing and rotatable relative to the housing.

In accordance with another aspect off the disclosure, an intramedullary intertrochanteric fracture fixation device includes an intramedullary nail, a neck screw and a set screw assembly. The intramedullary nail may include a proximal portion adjacent a proximal end and a distal portion adjacent a distal end. The proximal portion may define an angulated opening, an axial bore having a longitudinal axis that extends through the proximal end of the intramedullary nail and into the angulated opening, an internal threading, and a slot extending substantially parallel to the longitudinal axis. The neck screw may extend through the angulated opening and have an exterior surface with a groove and the set screw may be disposed within the axial bore of the intramedullary nail. The set screw may include a housing having an upper portion and a lower portion, the upper portion including a first end wall, a second end wall and a sidewall collectively defining a cavity. The set screw may include an external threading engaged with the internal threading, and the set screw may be disposed at least partially within the cavity of the housing such that rotation of the set screw rotates the set screw relative to the housing and causes the set screw and the housing to collectively move in the longitudinal direction.

In yet another aspect of the disclosure, an intramedullary intertrochanteric fracture fixation device includes an intramedullary nail, a neck screw and a set screw assembly. The intramedullary nail may have a proximal portion adjacent a proximal end and a distal portion adjacent a distal end. The proximal portion may define an angulated opening, an axial bore extending through the proximal end of the intramedullary nail and into the angulated opening, an internal threading, and a slot, the axial bore having a longitudinal axis. The neck screw may extend through the angulated opening, and the set screw assembly may be pre-operatively assembled within the proximal portion of the intramedullary nail, such that the set screw assembly is cannulated to receive a guidewire.

DETAILED DESCRIPTION

As used herein, when referring to the femur or the intramedullary nail, the term "proximal" means the end of femur or the intramedullary nail that is closer to the heart when the intramedullary nail is implanted within the medullary canal of a patient in its intended manner. The term "distal" means the end of femur or the intramedullary nail that is further from the heart when the intramedullary nail is implanted within the medullary canal of the patient as intended. The term "anterior" means towards the front part of the body or the face and the term "posterior" means towards the back of the body. The term "medial" means toward the midline of the body and the term "lateral" means away from the midline of the body. When referring to the neck screw, the term "rear" means closer to the user, whereas the term "front" means further from the user. Also as used herein, the terms "substantially," "generally" and "about" are intended to mean that slight deviations from absolute are included within the scope of the term so modified.

Throughout this disclosure, a fracture refers to a femoral neck fracture, however, the devices described hereinafter can be used to fixate associated fractures of the femoral shaft as well as factures in other long bones such as the tibia or the humorous, whether the fracture be naturally occurring or surgeon-induced.

Figure 1:
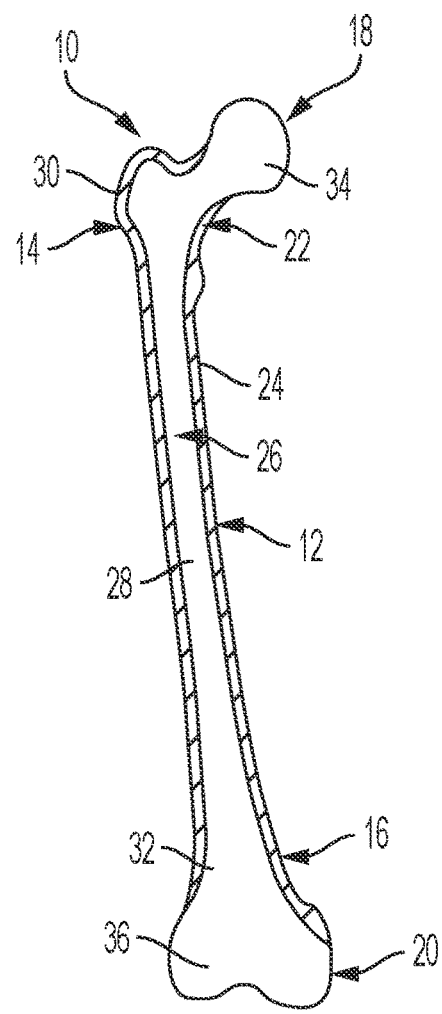
FIG. 1 is a cross section view of a femur.

FIG. 1 illustrates a femur 10 and its six anatomical regions: a diaphysis or midshaft 12, proximal metaphysis 14, distal metaphysis 16, proximal epiphysis or head 18, distal epiphysis 20, and a femoral neck 22. The femur 10 includes a hard cortex 24 and a medullary cavity 26. The medullary cavity 26 includes a medullary canal 28 which runs through the center of shaft 12, proximal and distal metaphyseal areas 30, 32, and the proximal and distal epiphyseal areas 34 and 36.

Figure 2:
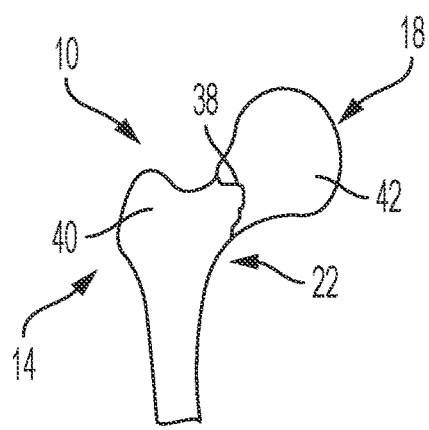
FIG. 2 is an anterior-posterior elevation view of a proximal femur having a femoral neck fracture.

FIG. 2 is an anterior-posterior view of a proximal portion of femur 10 having a fracture 38 extending along femoral neck 22. Fracture 38 separates the proximal femur into a first bone portion 40 located adjacent the proximal metaphysis 14 and a second bone portion 42 located adjacent the proximal epiphysis or head 18. Fracture 38 is an exemplary illustration of an unstable, extra-articular fracture, i.e., the fracture is located outside of a joint. This type of fracture, if not treated, can lead to long-term complications including comminution (i.e., pulverization of the bone), which may result in shortening of femoral neck 22 and severe pain.

Figure 3:
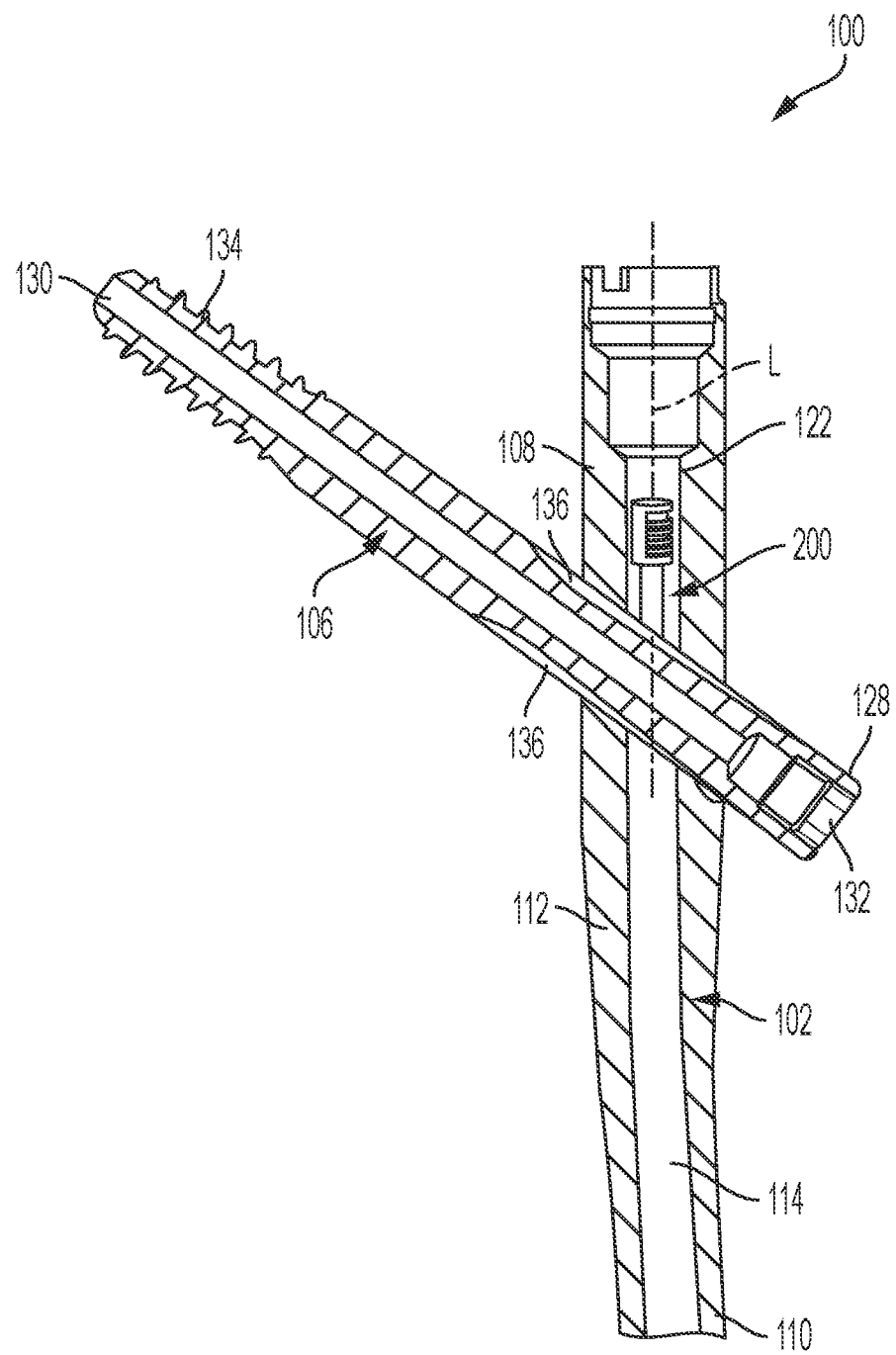
FIG. 3 is cross-section view of an intramedullary intertrochanteric fracture fixation device including an intramedullary nail, a neck screw and a set screw assembly according to an embodiment of the present disclosure.

FIG. 3 illustrates an intramedullary intertrochanteric fracture fixation device 100 according to an embodiment of the present disclosure. The device 100 is designed to compress first bone portion 40 and second bone portion 42 (shown in FIGS. 1 and 2) and maintain rotational stability between the first and second bone portions during healing of fracture 38. Device 100 includes an intramedullary nail 102 having an angulated opening 104 (shown in FIG. 4) extending through the nail in the lateral to medial direction, a neck screw 106 that is insertable through the angulated opening for compressing the fractured bone portions together and a set screw 200 for rotationally stabilizing the neck screw within the angulated opening of the intramedullary nail.

Figure 4:
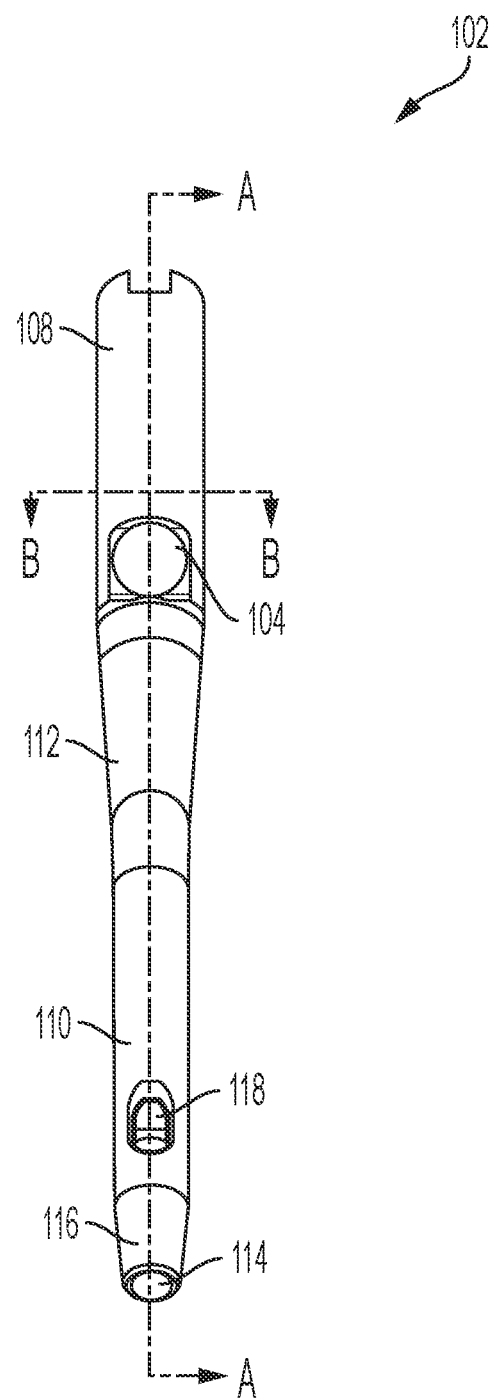
FIG. 4 is a lateral side perspective view of the intramedullary nail shown in FIG. 3.

With reference to FIG. 4, intramedullary nail 102 includes a rod-shaped body having a proximal portion 108, a distal portion 110 and an intermediate portion 112 located between and connecting the proximal and distal portions. The rod-shaped body of intramedullary nail 102 may be anatomically shaped to allow the intramedullary nail to be inserted into the medullary canal 28 of femur 10 (shown in FIG. 1). For this reason, intermediate portion 112 may be bent and tapered in the proximal to distal direction.

The rod-shaped body of intramedullary nail 102 is cannulated and defines a channel 114 that is configured to receive a surgical wire, such as a K-wire, for guiding the intramedullary nail into a proper position within the medullary canal 28 of the femur 10 (shown in FIG. 1). Intramedullary nail 102 may have a substantially circular cross-section over its entire length such that proximal portion 108 and distal portion 110 are substantially cylindrical. The proximal portion 108 of intramedullary nail 102 has a diameter sufficient to accommodate angulated bore 104. The distal portion 110 of intramedullary nail 102 has a diameter that is smaller than the diameter of proximal portion 108, and that is anatomically shaped to the medullary canal 28 of femur 10 to facilitate the insertion of the distal portion of the intramedullary nail into the medullary canal of the femur. For the same reason, the distal portion 110 of intramedullary nail 102 has a conical tip 116 at its distal end. The distal portion 110 of intramedullary nail 102 may also define an aperture 118 configured to receive a bone fastener such as a locking screw for fastening the intramedullary nail to the shaft 12 of femur 10 after implantation.

Figure 5A:
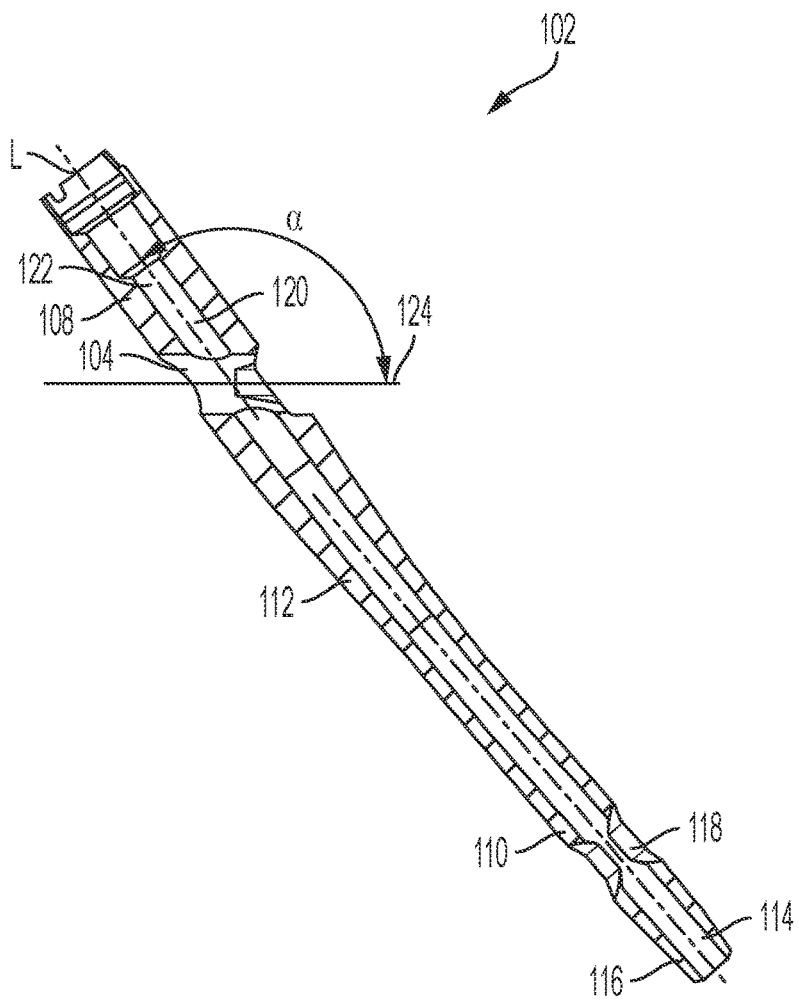
FIG. 5A is a cross-section view taken along line A-A of the intramedullary nail shown in FIG. 4.
Figure 5B:
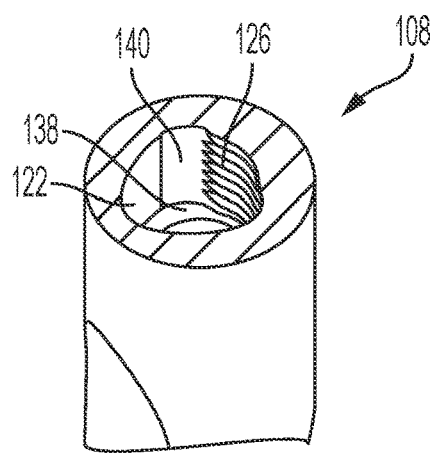
FIG. 5B is a cross-section view taken along line B-B of the intramedullary nail shown in FIG. 4.

As shown in FIGS. 5A and 5B, intramedullary nail 102 has an axial bore 122 that extends along a longitudinal axis L of the proximal portion 108 of the nail between the proximal end of the nail and angulated opening 104. Axial bore 122 includes internal threading 126 configured to mate with corresponding threading provided on set screw assembly 200 (shown in FIG. 3).

Angulated opening 104 defines a bore axis 124 that is transversely angled with respect to the longitudinal axis L of proximal portion 108 such that the bore axis of the angulated opening has an oblique extension relative to an axial extension of the proximal portion. In other words, bore axis 124 of angulated opening 104 is oriented obliquely with respect to the longitudinal axis L of the proximal portion 108. Thus, the bore axis 124 of angulated opening 104 is inclined at an angle α with respect to the longitudinal axis L of the proximal portion 108. Angle α may be between approximately 90° and approximately 140°, and may be, for example, about 126°.

Returning to FIG. 3, neck screw 106 extends through angulated opening 104 in a lateral to medial direction. As will be explained in more detail below, neck screw 106 is coupled to intramedullary nail 102, via set screw 200, in a manner that prevents the neck screw from rotating in angulated opening 104 and in a manner that allows the neck screw to limitedly slide along bore axis 124 (shown in FIG. 5A) to account for load shifting.

Neck screw 106 includes a rear end 128 and a front end 130. The rear end 128 of neck screw 106 includes a recess 132, for example, a hexalobular internal driving feature configured to receive a tool tip such as a screw driver or wrench. The front portion of neck screw 106 includes a thread 134, such as a coarse thread, for anchoring the neck screw into intertrochanteric bone. The peripheral surface of neck screw 106 defines a plurality of grooves 136 that extend in a direction generally parallel to the longitudinal axis of the neck screw. For example, neck screw 106 may include four grooves 136 circumferentially spaced about the peripheral surface of the neck screw at intervals of 90°. Each groove 136 defines a rising ramp having a shallow end and a deep end. The rising ramp extends from the rear portion of neck screw 106 toward the front portion of the neck screw. Because the longitudinal axis of neck screw 106 is substantially coaxial with the bore axis 124 of angulated opening 104, the neck screw is configured to transfer loads placed on the femoral head to the intramedullary nail 102, and at the same time, bridge the fracture 38 and compress first bone portions 40 and second bone portion 42 together.

Set screw assembly 200, as shown in FIGS. 6A-8, is cannulated and thus overcomes the drawbacks associated with the set screws described in the prior art, namely the difficulties associated with intraoperative assembly. Because set screw assembly 200 is cannulated, the set screw assembly can be pre-operatively assembled within intramedullary nail 102 and configured to receive a guidewire while disposed within the nail. That is, during operation, a surgeon may insert intramedullary nail 102, in which set screw assembly 200 is housed, over the guidewire and into position within the medullary canal of the patient. As used herein, the term "pre-operatively assembled" means that set screw assembly 200 is assembled within intramedullary nail 102 by the manufacturer before intertrochanteric fracture fixation device 100 is shipped, or alternatively, that the set screw assembly is assembled within the nail by a user before the nail is implanted into the medullary canal of a patient.

Figure 6A:
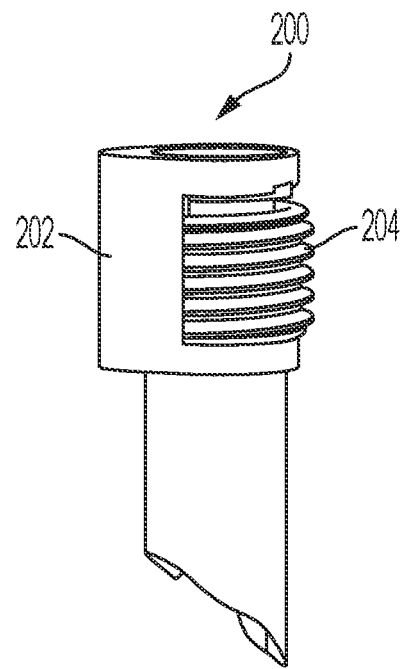
FIG. 6A is a side elevation view of the set screw assembly shown in FIG. 3.
Figure 6B:
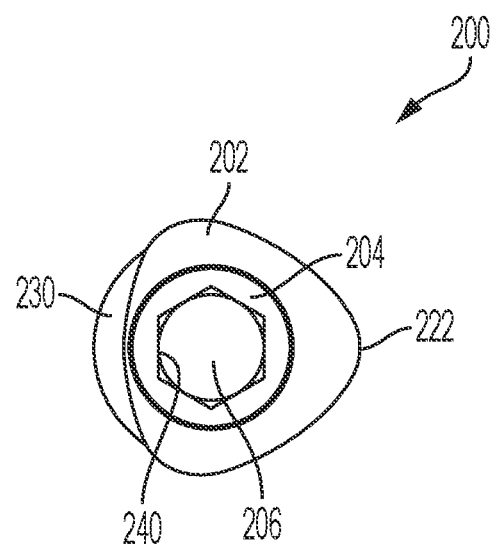
FIG. 6B is a top elevation view of the set screw assembly shown in FIG. 3.
Figure 8:
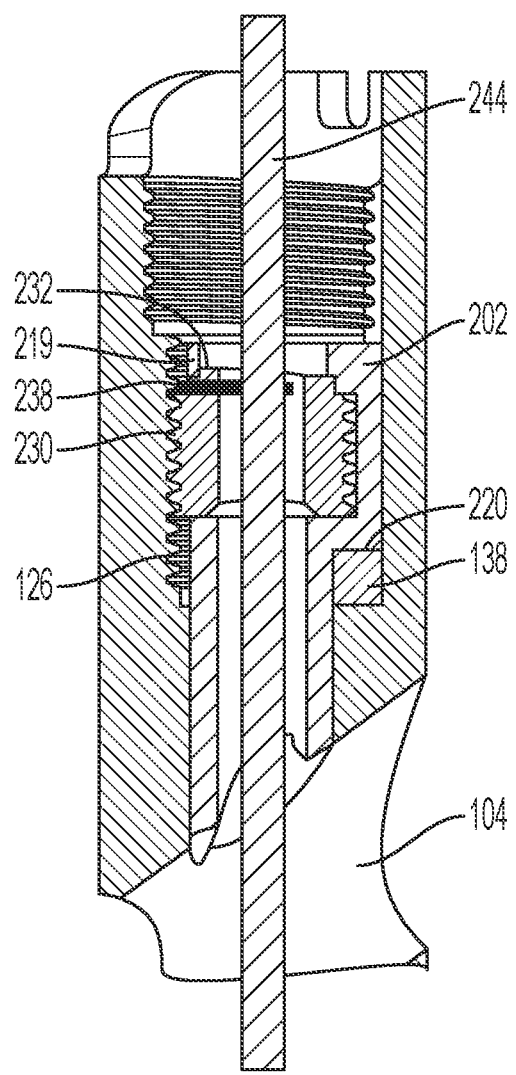
FIG. 8 is a partial cross-section view depicting a guidewire extending through the set screw assembly and the intramedullary nail shown in FIG. 3.

Set screw assembly 200 includes a housing 202 and a set screw 204. As shown in FIGS. 6B and 8, a cannulation 206 extends along a longitudinal axis of set screw assembly 200 and completely through the housing 202 and the set screw 204 of the set screw assembly such that when the set screw is disposed within the housing and pre-operatively assembled within intramedullary nail 102, the set screw assembly is configured to receive a guidewire.

Figure 7:
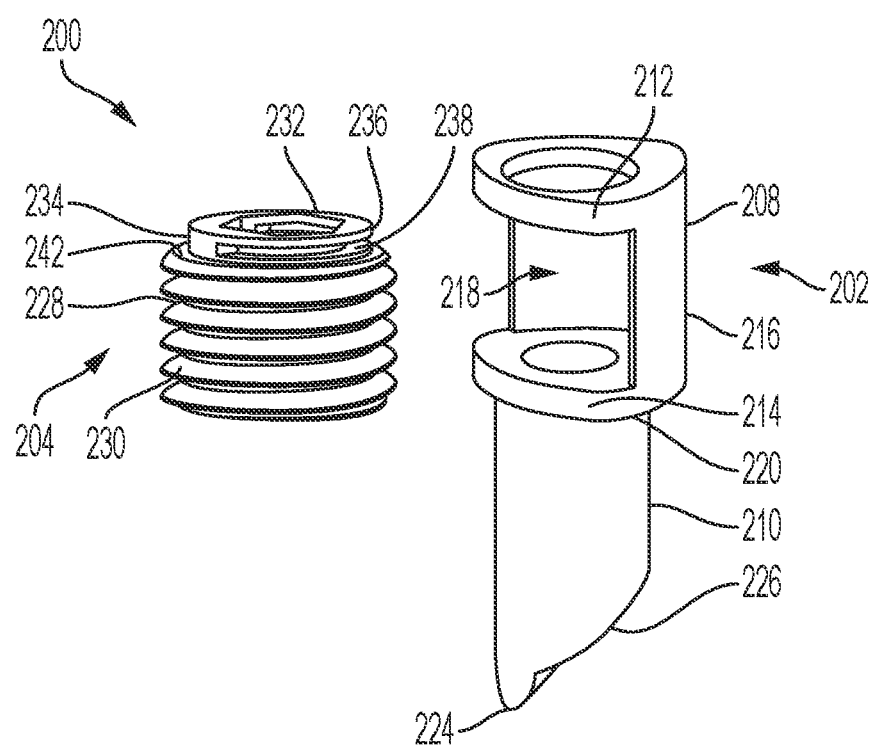
FIG. 7 is an exploded view of the set screw assembly shown in FIGS. 6A and 6B.

With reference to FIG. 7, housing 202 includes an upper portion 208 and a lower portion 210. The upper portion 208 of housing 202 includes a first end wall 212, a second end wall 214 spaced a distance from the first end wall, and a sidewall 216 that extends between the first and second end walls and partially surrounds the cannulation 206 of the upper portion. Put another way, sidewall 216 only partially surrounds the longitudinal axis of set screw assembly 200. In this manner, the combination of the first end wall 212, the second end wall 214 and the sidewall 216 of upper portion 208 defines a cavity 218 sized and configured to receive set screw 204. In a preferred embodiment, the first end wall 212 includes a lip 219, as shown in FIG. 8, for retaining set screw 204 within cavity 218.

The upper portion 208 of housing 202 has a transverse cross-section that is greater than a transverse cross-section of the lower portion 210 of the housing such that a ledge 220 is formed at the junction of the upper and lower portions. Additionally, the transverse cross-section of the upper portion 208 of housing 202 may be polygonal in shape. As used herein, the term "polygon" or "polygonal" is defined as any shape that is not completely circular and that includes one or more vertices 222. The vertices 222 may form a sharp point or be rounded. For example, as shown in FIG. 6B, the transverse cross-section of the upper portion 208 of housing 202 may be substantially triangular and include rounded vertices.

With additional reference to FIG. 5B, the proximal portion 108 of intramedullary nail 102 includes a seat 138 extending inwardly from the wall that defines the axial bore 122 of the intramedullary nail. The wall that defines axial bore 122 also defines a longitudinal slot 140 that extends substantially parallel to a longitudinal axis of the axial bore. Longitudinal slot 140 is shaped and sized to receive the corresponding vertices 222 of housing 202 and thus may act as a track for stabilizing set screw assembly 200 as the set screw assembly is loaded into intramedullary nail 102. Moreover, after set screw assembly 200 has been secured to intramedullary nail 102, the positioning of the vertices 222 within longitudinal slot 140 will inhibit unwanted post-operative rotation of the set screw assembly within axial bore 122.

The lower portion 210 of housing 202 is substantially cylindrical in shape and includes one or more protrusions 224 extending from a distal end 226 of the housing. Protrusion 224 is sized and shaped to extend into the angulated opening 104, and into one of the grooves 136 of neck screw 106. The distal end 226 of lower portion 210 may be angled obliquely with respect to the longitudinal axis of set screw assembly 200. In a preferred embodiment, the angle is approximately equal to α (e.g., the angle between the bore axis 124 of angulated opening 104 and the longitudinal axis L of the proximal portion 108 of nail 102) such that only protrusion 224 extends into the angulated opening 104 of intramedullary nail 102 when the ledge 220 of housing 202 contacts seat 138. In other words, the distal end 226 of the lower portion 210 of housing 202 does not extend into the angulated opening 104 of intramedullary nail 102 and will not contact a peripheral surface of neck screw 106.

Set screw 204 has a substantially cylindrical body 228 provided with an external threading 230 disposed about the body. Set screw 204 is sized to be at least partially received within the cavity 218 of housing 202 in a manner that allows the threading 230 of the set screw to protrude from the cavity (as shown in FIG. 6B) and to engage the internal threading 126 of intramedullary nail 102 (as shown in FIG. 8) to threadably mate set screw assembly 200 to the intramedullary nail.

Set screw 204 includes an elastic member 232 that is transitionable between an expanded condition (e.g., uncompressed) and a compressed condition. In the compressed condition, set screw 204 has a length in the axial direction that is equal to or less than the distance between the first end wall 212 and the second end wall 214 of housing 202. Thus, when elastic member 232 is in the compressed condition, set screw 204 can be inserted into cavity 218. On the other hand, when elastic member 232 is expanded, the axial length of set screw 204 is greater than the distance between the first end wall 212 and the second end wall 214 of housing 202. As a result, when set screw 204 is disposed within cavity 218 and elastic member 232 is expanded into a friction fit engagement with the first end wall 212 and the second end wall 214 of housing 202, the set screw is securely coupled to the housing, and lateral movement of the set screw relative to the housing is prevented. The engagement between set screw 204 and housing 202 also prevents the set screw from unintentionally rotating within the housing and requires increased torque to intentionally rotate the set screw.

Elastic member 232 may have a transverse cross-section that is smaller than a transverse cross-section of the body 228 of set screw 204 such that a retaining step 242 is formed about the elastic member. Retaining step 242 may engage with the lip 219 of the housing to inhibit lateral movement of set screw 204 relative to housing 202 and aid in securely coupling the set screw within cavity 218.

As shown in FIG. 7, elastic member 232 is a flange that is integrally formed, or otherwise attached, to a terminal end of set screw 204. The flange has a first or attached end 234, and a second or unattached end 236. The first end 234 of the flange extends from a terminal end of the body 228 of set screw 204 on a first lateral side of cannulation 206, and the flange extends across the cannulation of the set screw such that the second or unattached end 236 is disposed over the terminal end of the set screw on an opposing lateral side of the cannulation. Because the second end 236 of the flange is not attached to the body 228 of set screw 204, a gap 238 is formed between the second end (e.g., the unattached end) of the flange and the terminal end of the body to form a cantilever.

The flange may be formed of any material that exhibits elasticity such as a metal, a metal alloy or a rubber. In this manner, when a distally directed force is applied to the second end 236 of the flange, for example, by the first end wall 212 of housing 202 during insertion of set screw 204 into cavity 218, the second end of the flange will compress toward the terminal end of the body 228 of set screw 204, thereby decreasing the size of gap 238 and the axial length of the set screw 202. After set screw 204 has been inserted into cavity 218, beyond lip 219, the elastic material will expand to secure the set screw within the cavity.

The above described flange is merely an example of elastic member 232 and it will be understood that any other elastic member such as a spring, rubber, silicon or the like may be substituted in place of the flange. Moreover, elastic member 232 may be integrally formed as a component of a monolithic set screw 204 or otherwise attached to a separate body of set screw 204 or housing 202, so long as the compression and expansion of the elastic member securely couples the set screw within the cavity 218 of the housing, and permits the set screw to rotate within the cavity when a rotational force is applied to the set screw.

Referring to FIG. 6B, elastic member 232 and/or the cannulation 206 of set screw 204 defines a driving feature 240, such as a recessed hexalobular internal driving feature, adapted to receive a tool tip, for example, a screw driver or a hex key (not shown), to rotate the set screw in a first direction and thread set screw assembly 200 into axial bore 122 in a distal direction and into connection with intramedullary nail 102. Of course, the tool tip may also be inserted into driving feature 240 and rotated in a second direction, opposite to the first direction, to move set screw 204 thorough axial bore 122 in a proximal direction to unthread the set screw from intramedullary nail 102.

Use of intramedullary intertrochanteric fracture fixation device 100 to heal fracture 38 is now described. First, set screw assembly 200 is assembled by inserting set screw 204 into the cavity 218 of housing 202. During insertion, the elastic member 232 of set screw 204 will transition from the uncompressed condition to the compressed condition when the elastic member contacts the first end wall 212 of housing 202. More particularly, the first end wall 212 of housing 202 will apply a distally directed force to the unattached end 236 of flanged elastic member 232 and compress the unattached end toward the terminal end of the body 228 of set screw 204. This compression reduces the size of gap 238 and, in turn, the axial length of set screw 204 (e.g., measured from the unattached end 236 of the flange to an opposing terminal end of body 228), and allows the set screw to enter cavity 218. After set screw 204 has passed beyond the lip 219 of the upper portion 208 of housing 202, the elastic member 232 elastically expands. In the uncompressed condition, lip 219 sits within retaining step 242 and frictionally secures set screw 204 within cavity 218. The engagement between lip 219 and retaining step 242 inhibits lateral movement of the set screw 204 relative to housing 202, while permitting the set screw to rotate about its longitudinal axis within cavity 218 when a rotational force is applied to the set screw.

Set screw assembly 200 may then be pre-operatively assembled within the proximal portion 108 of intramedullary nail 102. To begin, the manufacturer or another user may position one of the vertices 222 of housing 202 into the longitudinal slot 140 of intramedullary nail 102. Once positioned, set screw assembly 200 may be slid in a distal direction until the external threading 230 of set screw 204 engages the internal threading 126 of intramedullary nail 102. Sliding set screw assembly 200 into the axial bore 122 of intramedullary nail 102 as described will prevent the set screw assembly from tilting relative to the longitudinal axis and thus assists in properly aligning the external threading 230 of set screw 204 and the internal threading 126 of the intramedullary nail. The likelihood that either thread will be damaged during threading of screw 204 to intramedullary nail 102 is thereby reduced.

A driving tool (not shown) may then be inserted into the recessed driving feature 240 of set screw 204 and rotated in a first direction (e.g., clockwise) to threadably mate the set screw and intramedullary nail 102 and cause set screw assembly 200 to move in a distal direction within axial bore 122. During rotation of the set screw 204, components of set screw assembly 200 and intramedullary nail 102 may interact in several ways: 1) the engagement between the vertices 222 of housing 202 and the longitudinal slot 140 of the intramedullary nail prevents the housing from rotating within the axial bore; 2) the engagement between expanded set screw 204 and the housing (including the engagement between the lip 219 of the housing and the retaining step 242 of the set screw) prevents the set screw from moving in an axial or lateral direction relative the cavity 218 of the housing (while permitting rotational movement of the set screw within the cavity); and 3) the engagement between the external threading 230 of the set screw 204 and the internal threading 126 of the intramedullary nail 102 causes the set screw and, in turn, the housing 202 to move in a distal direction within axial bore 122. Rotation of set screw 204 may be ceased before the protrusions 224 of lower portion 210 extend into the angulated opening 104 of intramedullary nail 102.

With intramedullary intertrochanteric fracture fixation device 100 prepared for surgery, a surgeon may then advance the intramedullary nail 102 over a guidewire 244, through the cannulated set screw assembly 200 (as shown in FIG. 8), and into position within the medullary canal 28 of the patient. After intramedullary nail 102 has been positioned within the medullary canal 28 of femur 10, the surgeon may remove guidewire 244 and insert neck screw 106 through the angulated opening 104 of the intramedullary nail in order to compress the fractured bone portions together.

After the surgeon has confirmed that neck screw 106 is appropriately positioned within the intertrochanteric bone, the driving tool may then again be used to rotate set screw 204 and drive set screw assembly 200 in the distal direction until the ledge 220 of housing 202 engages the seat 138 of intramedullary nail 102 such that protrusion 224 extends into the angulated opening 104 of the intramedullary nail, and into one of the grooves 136 of neck screw 106. Once positioned within groove 136, protrusion 224 prevents neck screw 106 from rotating about bore axis 124, and effectively prevents neck screw 106 from rotating within angulated opening 104.

The surgeon may then optionally choose to limit the axial movement of neck screw 106 relative to intramedullary nail 102. In order to set this limit, the surgeon may intraoperatively use the driving tool to rotate set screw 204 until the desired limit has been reached. If the surgeon desires to decrease the axial movement of neck screw 106, the surgeon may rotate the driving tool in a first direction (e.g., clockwise) causing set screw assembly 200 to move distally within axial bore 122 as described above. As a result, protrusion 224 will project further into the ramped groove 136 of neck screw 106 and limit the distance that the neck screw is able to slide. If protrusions 224 are secured into firm engagement with a surface of the neck screw 106 that defines groove 136, movement of the neck screw may be prevented all together.

On the other hand, if the surgeon desires to allow or increase the axial sliding of neck screw 106, the surgeon may intraoperatively rotate set screw 204 in a second direction (e.g., counter clockwise) causing set screw assembly 200 to move in a proximal direction. Such movement will result in the retraction of protrusion 224 away from neck screw 106 and permit the neck screw to slide relatively further in the axial direction before contacting the ramped grooves 136 of the neck screw.

Figure 9A:
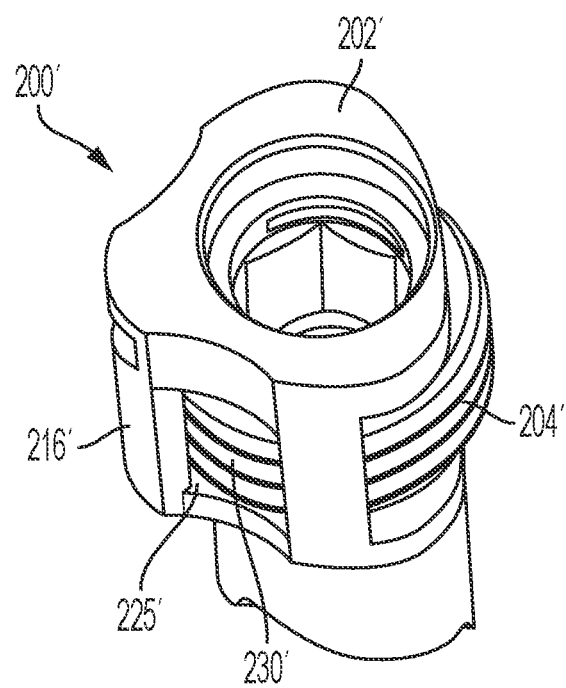
FIG. 9A is a perspective view of a set screw assembly according to another embodiment of the present disclosure.
Figure 9B:
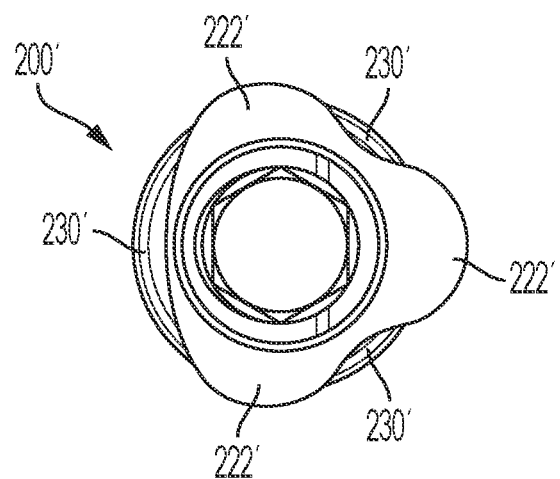
FIG. 9B is a plan view of the set screw assembly of FIG. 9A.
Figure 9C:
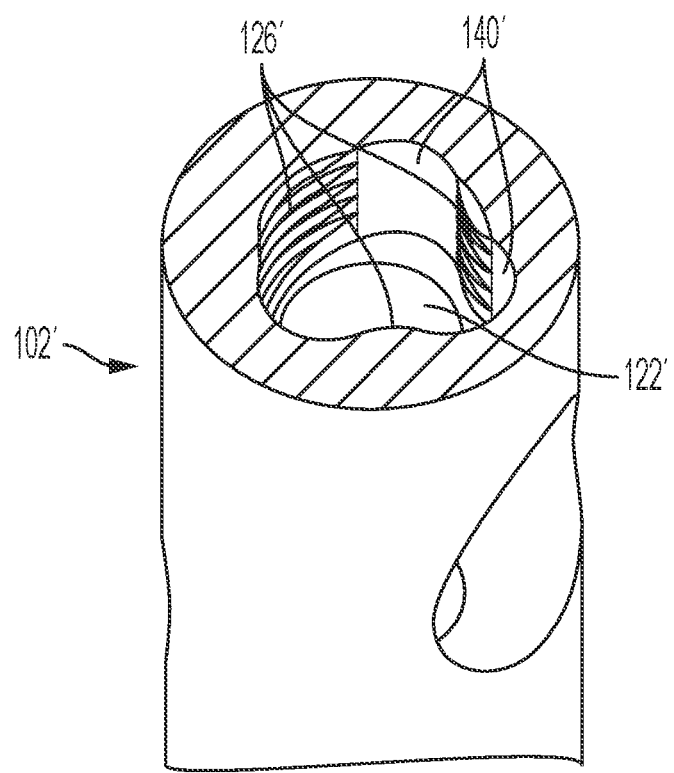
FIG. 9C is a cross-section view taken orthogonal to the longitudinal axis of an intramedullary nail configured to receive the set screw assembly of FIGS. 9A and 9B according to another embodiment of the present disclosure.
Figure 9D:
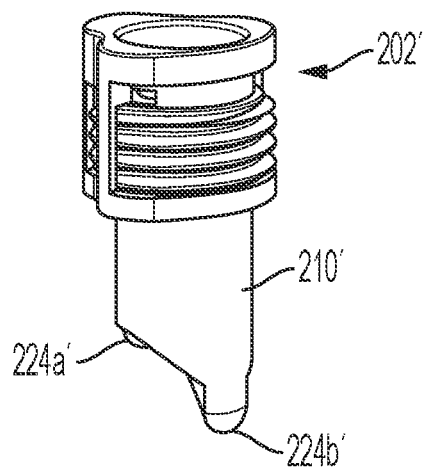
FIGS. 9D and 9E are a perspective view and a posterior-anterior side elevation view, respectively, of a modified embodiment of set screw assembly of FIGS. 9A and 9B.
Figure 9E:
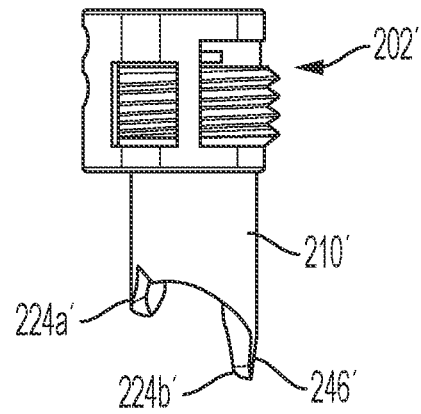
Figure 9F:
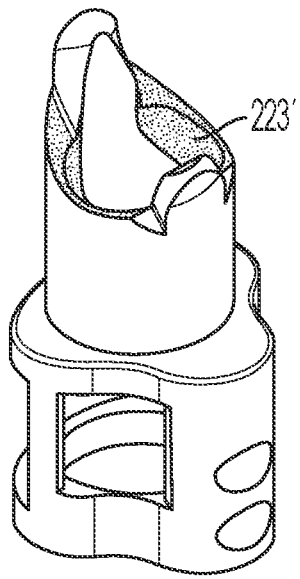
FIGS. 9F and 9G are bottom perspective views of the housing of the modified embodiment of the set screw assembly of FIGS. 9D and 9E.
Figure 9G:
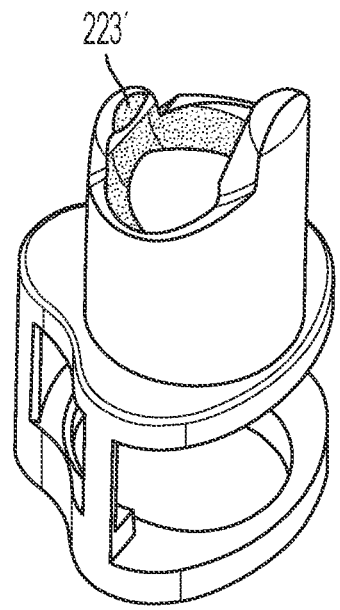

FIGS. 9A-9C illustrate a variant intramedullary nail 102' and a variant set screw assembly 200'. Intramedullary nail 102' and set screw assembly 200' include all of the features described above with respect to intramedullary nail 102 and set screw assembly 200 of intramedullary intertrochanteric fracture fixation device 100 and are further modified as described below. The sidewall 216' of housing 202', for example, includes a pair of concave cutouts that define apertures 225' which allow the external threading 230' of set screw 204' to extend through the apertures and into direct engagement with the internal threading 126' of intramedullary nail 102' when set screw assembly 200' is disposed within axial bore 122'. With specific reference to FIG. 9B, housing 202' has a substantially triangular and three-leaf clover cross-section shape taken orthogonal to the longitudinal axis.

The lower portion of housing 202' may be formed substantially similar to housing 202 shown in FIGS. 6A-8. Alternatively, as shown in FIGS. 9D-9H, the lower portion 210' of housing 202' may be cylindrical in shape and include a distal end 226' formed by one or more outwardly tapered surfaces 223' that facilitate insertion of the k-wire through set screw assembly 200'. The distal end 226' of housing 202' also includes a medial protrusion 224a' and a lateral protrusion 224b'. Medial and lateral protrusions 224a', 224b' are curved and, more specifically, parabolic in shape when viewed from a medial-lateral perspective. The curved shape is designed to reduce stress on protrusions 224a', 224b' when the protrusions engage neck screw 106'.

Figure 9H:
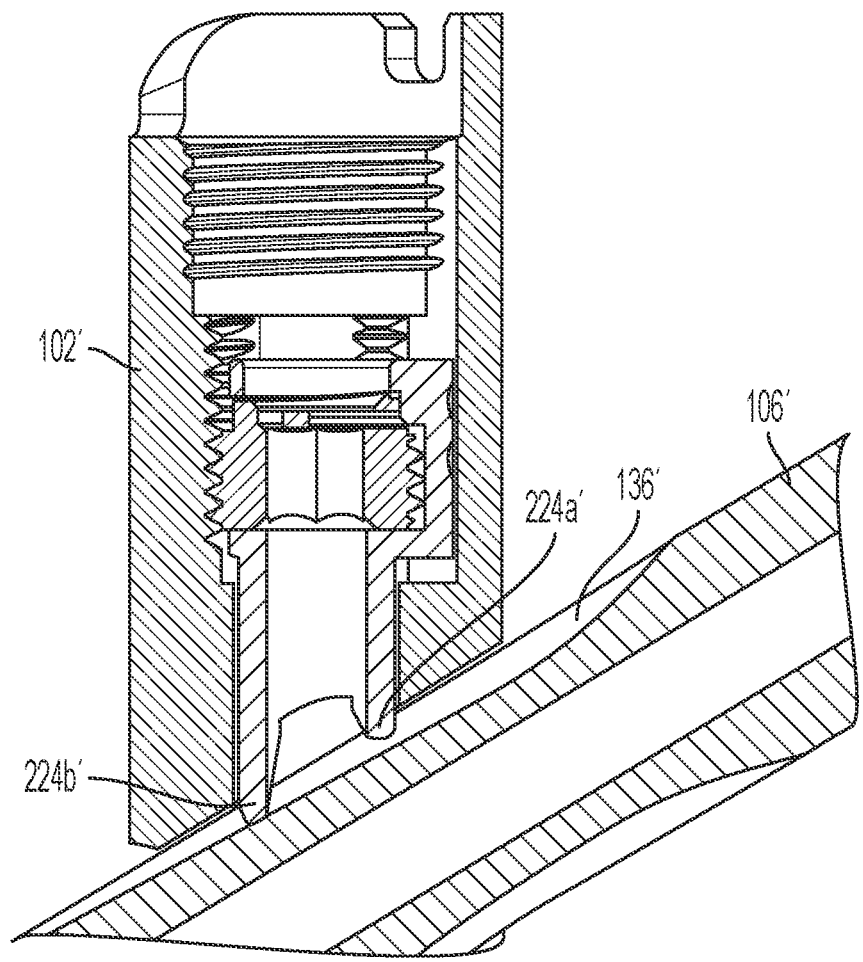
FIG. 9H is a cross-section view taken along the longitudinal axis illustrating the engagement between a neck screw and the set screw assembly of FIGS. 9D and 9E.

Lateral protrusion 224b' extends further in a distal direction than medial protrusion 224a'. Thus, when the fracture fixation device is assembled as shown in FIG. 9H and the medial and lateral protrusions 224a', 224b' are disposed within the groove 136' of neck screw 106', the lateral protrusion engages a bottom surface of the groove and causes the medial protrusion to float above the bottom surface of the groove. Put differently, medial protrusion 224a' extends partially into groove 136' to prevent neck screw 106' from rotating within the axial bore but does not engage the bottom surface of the groove and, therefore, will not necessarily slide against the bottom surface of the groove as the neck screw limitedly slides along the bore axis. Consequently, medial protrusion 224a' will not deform.

Lateral protrusion 224b' includes a chamfer 246' extending in the lateral-to-medial direction. The chamfer 246' of lateral protrusion 224b' is designed to anticipate and prevent plastic deformation of the lateral protrusion as the protrusion slides laterally against the bottom surface of the groove 136' of neck screw 106'.

Referring to FIG. 9C, it will be understood that the axial bore 122' of intramedullary nail 102' may be modified (relative to the axial bore 122 of intramedullary nail 102) to correspond to the three-leaf clover shape of housing 202'. For example, axial bore 122' may include three longitudinal slots 140' shaped and sized to receive a respective leaf or vertices 222' of housing 202'. Like longitudinal slot 140, each of longitudinal slots 140' may act as a track for stabilizing set screw assembly 200' as the set screw assembly is loaded into intramedullary nail 102' and inhibiting unwanted post-operative rotation of the set screw assembly after the set screw assembly has been positioned within axial bore 122'. Moreover, axial bore 122' includes an internal threading 126' disposed between each adjacent pair of longitudinal slots 140'. In this manner, the alignment and threading of set screw assembly 200' to intramedullary nail 102' may be improved. The modified fracture fixation device shown in FIGS. 9A-9H can be used as described above with respect to intramedullary intertrochanteric fracture fixation device 100 and, therefore, is not described again in detail herein.

Figure 10A:
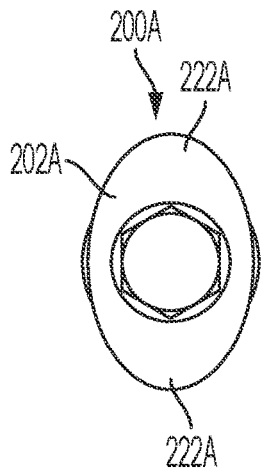
FIGS. 10A-10F are top elevation views of example set screw assemblies according to other embodiments of the present disclosure.
Figure 10B:
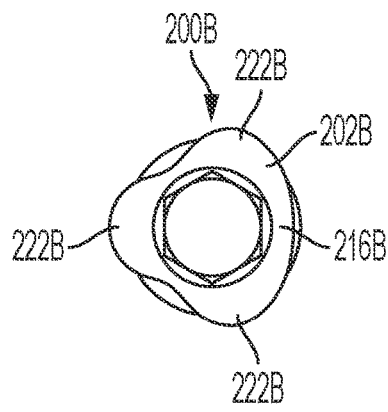
Figure 10C:
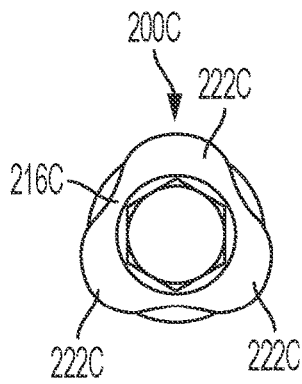

FIGS. 10A-10C are top elevation views of example set screw assemblies 200A-200F in accordance with other embodiments of the present disclosure. Each one of set screw assemblies 200A-200F includes all of the features of set screw assembly 200 and/or set screw assembly 200' with the only difference being the shape of the housing. The term "shape," as used below with respect to housings 202A-202F, refers to the shape of the cross-section of the housing taken orthogonal to the longitudinal axis.

Each set screw assembly 200A-200F is preferably designed to be used with a different intramedullary nail (not shown) having an axial bore that corresponds in shape to the shape of the respective housing 202A-202F. More specifically, each housing 202A-202F has a polygonal shape with a number of vertices that is equal to the number of longitudinal slots within the axial bore of the corresponding intramedullary nail. In this regard, each one of the vertices can be positioned within a respective one of the longitudinal slots to stabilize the set screw assembly when the set screw assembly is loaded into the corresponding intramedullary nail and to inhibit unwanted post-operative rotation of the set screw assembly after the set screw assembly has been positioned within the axial bore of the intramedullary nail.

FIG. 10A, for example, illustrates a set screw assembly 200A having a housing 202A shaped substantially as an oval and, more specifically, an ellipse with two diametrically opposed vertices 222A. Thus, the axial bore of its corresponding intramedullary nail (not shown) may be formed with two longitudinal slots positioned on opposite sides of the axial bore from one another.

The housing 202B of set screw assembly 200B, as shown in FIG. 10B, is similar in shape to the housing 202' of set screw assembly 200'. That is, the housing 202B of set screw assembly 200B is shaped substantially as a three-leaf clover and, includes three vertices 222B. The housing 202B of set screw assembly 200B, however, has a slightly thicker sidewall 216B compared to the sidewall 216' of set screw assembly 200'. Nevertheless, the corresponding intramedullary nail may be formed substantially as shown in FIG. 9C with three longitudinal slots angularly spaced about the axial bore.

FIG. 10C illustrates a third example housing 202C that is substantially triangular in shape and similar to the housing 202 of set screw assembly 200. The primary difference being that the sidewall 216C of housing 202C defines an arcuate cutout between each one of the three vertices 222C. Therefore, the intramedullary nail that corresponds to set screw assembly 200C may have an axial bore provided with three longitudinal slots angularly spaced about the axial bore.

Figure 10D:
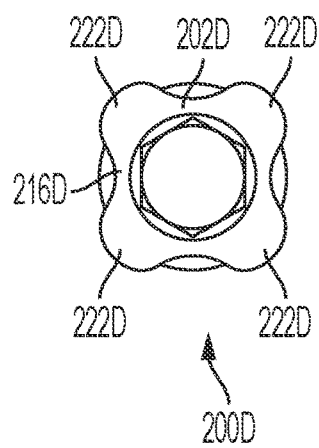

Referring now to FIG. 10D, the shape of the housing 202D is substantially rectangular and, more specifically, square. The sidewall 216D of housing 202D may define an arcuate cutout between any one of the adjacent four vertices 222D. In this regard, the intramedullary nail corresponding to set screw assembly 200D will define four longitudinal slots spaced 90 degrees from one another about the axial bore.

Figure 10E:
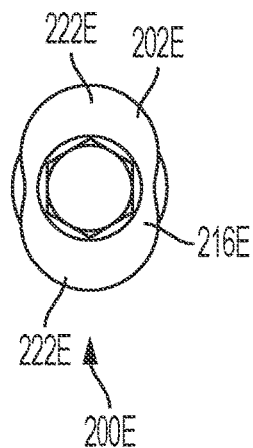

As shown in FIG. 10E, the housing 202E of set screw assembly 200E is shaped approximately as an ellipse with two diametrically opposed vertices 222E. The sidewall 216E of housing 202E may define two arcuate cutouts positioned along the minor axis of the housing. Therefore, the corresponding intramedullary nail may define two longitudinal slots positioned on opposite sides of the axial bore from one another.

Figure 10F:
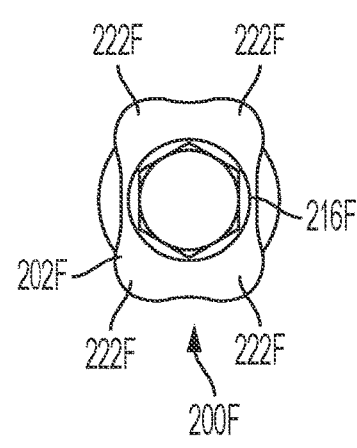

Turning to FIG. 10F, the housing 202F of set screw assembly 200F is shaped substantially as a rectangle with four vertices 222F and a thickened sidewall 216F along its width and a thinner sidewall along its length. Of course, the thickness of sidewall 216F may be altered and/or varied along the width and/or along the length of housing 202F. The corresponding intramedullary nail thus preferably has four longitudinal slots spaced 90 degrees about the axial bore from one another.

Although FIGS. 10A-10F illustrate the housings as specific shapes, it will be understood that the shape of the housing may be alternatively formed as any polygonal shape. Moreover, while the number of vertices of the respective housings is preferably equal to the number of longitudinal slots formed within the axial bore of a corresponding intramedullary nail, it will be appreciated that the number of vertices of the respective housings need not be equal to the number of longitudinal slots defined in the axial bore of a particular intramedullary nail. So long as one of the plurality of vertices of the housing is positioned within a single longitudinal slot of the intramedullary nail, the set screw assembly will exhibit some degree of stabilization during loading and the ability to withstand post-operative rotational forces, albeit to a lesser degree than if the number of vertices is equal to the number of longitudinal slots.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present disclosure as defined by the appended claims.

The invention claimed is:

1. A set screw assembly having a longitudinal axis for intramedullary fracture fixation devices, comprising:
   a set screw including a body with an external thread and an elastic member extending from the body, the elastic member having an uncompressed condition and a compressed condition; and
   a housing including a sidewall and first and second end walls extending from the sidewall in a transverse direction to the longitudinal axis, wherein the sidewall partially surrounds the longitudinal axis, and the combination of the first end wall, the second end wall, and the sidewall defines a cavity sized and configured to receive the set screw,
   wherein when the elastic member is in the compressed condition, the cavity is configured to allow the set screw to be inserted into the cavity,
   wherein when the set screw is inserted into the cavity and disposed within the cavity, the cavity is configured such that the elastic member is in the uncompressed condition and that the set screw is secured to the housing and rotatable about the longitudinal axis relative to the housing, and
   wherein the sidewall of the housing defines an aperture and a portion of the external thread of the set screw extends through the aperture and protrudes outside of the cavity when the set screw is secured to the housing.

2. The set screw assembly of claim 1, wherein the housing and the set screw are cannulated such that the set screw assembly is configured to receive a guide wire.

3. The set screw assembly of claim 1, wherein the elastic member comprises a cantilever flange having a first end attached to a terminal end of the body and a second end disposed above the terminal end of the body such that a gap is formed between the second end of the cantilever flange and the terminal end of the body.

4. The set screw assembly of claim 1, wherein when the elastic member is in the uncompressed condition, the set screw has a length in a direction along the longitudinal axis that is greater than a distance between the first and second end walls, and when the elastic member is in the compressed condition, the length of the set screw in the direction along the longitudinal axis is equal to or less than the distance between the first and second end walls.

5. The set screw assembly of claim 1, wherein the sidewall of the housing defines a plurality of discrete apertures and a portion of the external thread of the set screw extends through each of the apertures when the set screw is secured to the housing.

6. The set screw assembly of claim 1, wherein a lower portion of the housing comprises at least one protrusion extending distally from a distal end of the housing.

7. The set screw assembly of claim 6, wherein the at least one protrusion comprises a medial protrusion having a first length and a lateral protrusion having a second length longer than the first length.

8. An intramedullary fracture fixation device, comprising:
an intramedullary nail having a proximal portion adjacent a proximal end, the proximal portion defining an angulated opening, and an axial bore extending through the proximal end of the intramedullary nail and into the angulated opening, the axial bore having a longitudinal axis and an internal threading;
a neck screw configured to extend through the angulated opening; and
the set screw assembly of claim 1 pre-operatively assembled within the proximal portion of the intramedullary nail, the set screw assembly being cannulated to receive a guidewire.

9. The device of claim 8, further comprising a guidewire configured to extend into the axial bore of the intramedullary nail and through the set screw assembly.

10. An intramedullary fracture fixation device, comprising:
an intramedullary nail having a proximal portion adjacent a proximal end and a distal portion adjacent a distal end, the proximal portion defining an angulated opening, and an axial bore extending through the proximal end of the intramedullary nail and into the angulated opening, the axial bore having a longitudinal axis, an internal threading, and at least one slot extending substantially parallel to the longitudinal axis;
a neck screw configured to extend through the angulated opening and having an exterior surface with a groove; and
a set screw assembly having a longitudinal axis and configured to be disposed within the axial bore of the intramedullary nail, the set screw assembly comprising:
a set screw having a body with an external thread and an elastic member extending from the body, the elastic member having an uncompressed condition and a compressed condition; and
a housing including an upper portion and a lower portion, the upper portion including a sidewall and first and second end walls extending from the sidewall in a transverse direction to the longitudinal axis of the set screw assembly, and the combination of the first end wall, the second end wall, and the sidewall defining a cavity sized and configured to receive the set screw, wherein the sidewall partially surrounds the longitudinal axis of the set screw assembly; and
wherein when the elastic member is in the compressed condition, the cavity is configured to allow the set screw to be inserted into the cavity,
wherein when the set screw is inserted into the cavity and disposed within the cavity, the cavity is configured such that the elastic member is in the uncompressed condition and that the set screw is secured to the housing and rotatable about the longitudinal axis of the set screw assembly relative to the housing,
wherein the sidewall of the housing defines an aperture and a portion of the external thread of the set screw extends through the aperture and protrudes outside of the cavity when the set screw is secured to the housing, and
wherein when the set screw is partially disposed within the cavity of the housing and the set screw assembly is disposed within the axial bore of the intramedullary nail, the external threading of the set screw is engaged with internal threading of the axial bore such that rotation of the set screw rotates the set screw about the longitudinal axis of the set screw assembly and relative to the housing and causes the set screw assembly to move along the longitudinal axis of the axial bore of the intramedullary nail.

11. The device of claim 10, wherein a transverse cross-section of the upper portion of the housing is a polygon with at least one vertex positioned within the at least one slot to prevent rotation of the housing relative to the intramedullary nail when the set screw is rotated.

12. The device of claim 11, wherein the polygon comprises "n" number of vertices and wherein the at least one slot comprises a number of slots equal to "n".

13. The device of claim 10, wherein a transverse cross-section of the upper portion of the housing is greater than a transverse cross-section of the lower portion of the housing forming a ledge at a junction between the upper and lower portions of the housing.

14. The device of claim 13, wherein the proximal portion of the intramedullary nail includes a seat projecting inwardly into the axial bore for contacting the ledge of the housing and limiting distal movement of the housing within the axial bore.

15. The device of claim 14, wherein the lower portion of the housing further comprises a protrusion and wherein the lower portion of the housing includes a distal end angled with respect to the longitudinal axis of the set screw assembly such that when the ledge of the housing is in contact with the seat of the intramedullary nail only the protrusion extends into the angulated opening.

16. The device of claim 10, wherein the set screw is sized such that insertion of the set screw into the cavity causes the elastic member to contact one of the first or second end walls and transition to the compressed condition.

* * * * *